United States Patent [19]

Morgenstern

[11] Patent Number: 5,038,759

[45] Date of Patent: Aug. 13, 1991

[54] CERVICAL ORTHOPEDIC DEVICE

[75] Inventor: Walter R. Morgenstern, Miami, Fla.

[73] Assignee: Walthen Industries, Inc., Miami, Fla.

[21] Appl. No.: 357,256

[22] Filed: May 26, 1989

[51] Int. Cl.⁵ .............................................. A61H 1/02
[52] U.S. Cl. .................................. 128/75; 128/87 B; 128/DIG. 23
[58] Field of Search ................ 128/75, 87 B, DIG. 23

[56] References Cited

U.S. PATENT DOCUMENTS

| | | | |
|---|---|---|---|
| Re. 32,219 | 8/1986 | Garth .................... | 128/87 B X |
| D. 248,872 | 8/1978 | Thomas .................. | 128/DIG. 23 X |
| 3,055,358 | 9/1962 | DiPalma et al. ......... | 128/75 |
| 3,477,425 | 11/1969 | Grassl ..................... | 128/75 |
| 3,916,885 | 11/1975 | Gaylord, Jr. ............ | 128/87 B X |
| 3,921,626 | 11/1975 | Neel ....................... | 128/75 |
| 4,205,667 | 6/1980 | Gaylord, Jr. ............ | 128/75 |
| 4,413,619 | 11/1983 | Garth . | |
| 4,502,471 | 3/1985 | Owens ................... | 128/87 B X |
| 4,520,801 | 6/1985 | Lerman .................. | 128/87 B X |
| 4,538,597 | 9/1985 | Lerman .................. | 128/87 B X |
| 4,677,969 | 7/1987 | Calabrese ............... | 128/87 B X |
| 4,708,129 | 11/1987 | Pujals, Jr. . | |
| 4,712,540 | 12/1987 | Tucker et al. .......... | 128/75 X |
| 4,886,052 | 12/1989 | Calabrese ............... | 128/DIG. 23 X |

*Primary Examiner*—Richard J. Apley
*Assistant Examiner*—Linda C. M. Dvorak
*Attorney, Agent, or Firm*—Fleit, Jacobson, Cohn, Price, Holman & Stern

[57] ABSTRACT

An injection molded front section of a cervical collar having a chin support attached thereto along an upper edge portion opposite a lower padded edge portion, is adjustably positioned on a patient by a flexible strap underlying a back section releasably locked in overlapping relation to padded end portions of the front section. A stabilizing contact section is attached to the back section and projects from its upper edge portion to stabilize support of the collar on a patient in its adjusted position. The front and back sections of the collar are color coded during formation in accordance with size and corresponding thickness determined to provide optimum stiffness accommodating bending of the collar during installation and orthopedic support once applied.

16 Claims, 3 Drawing Sheets

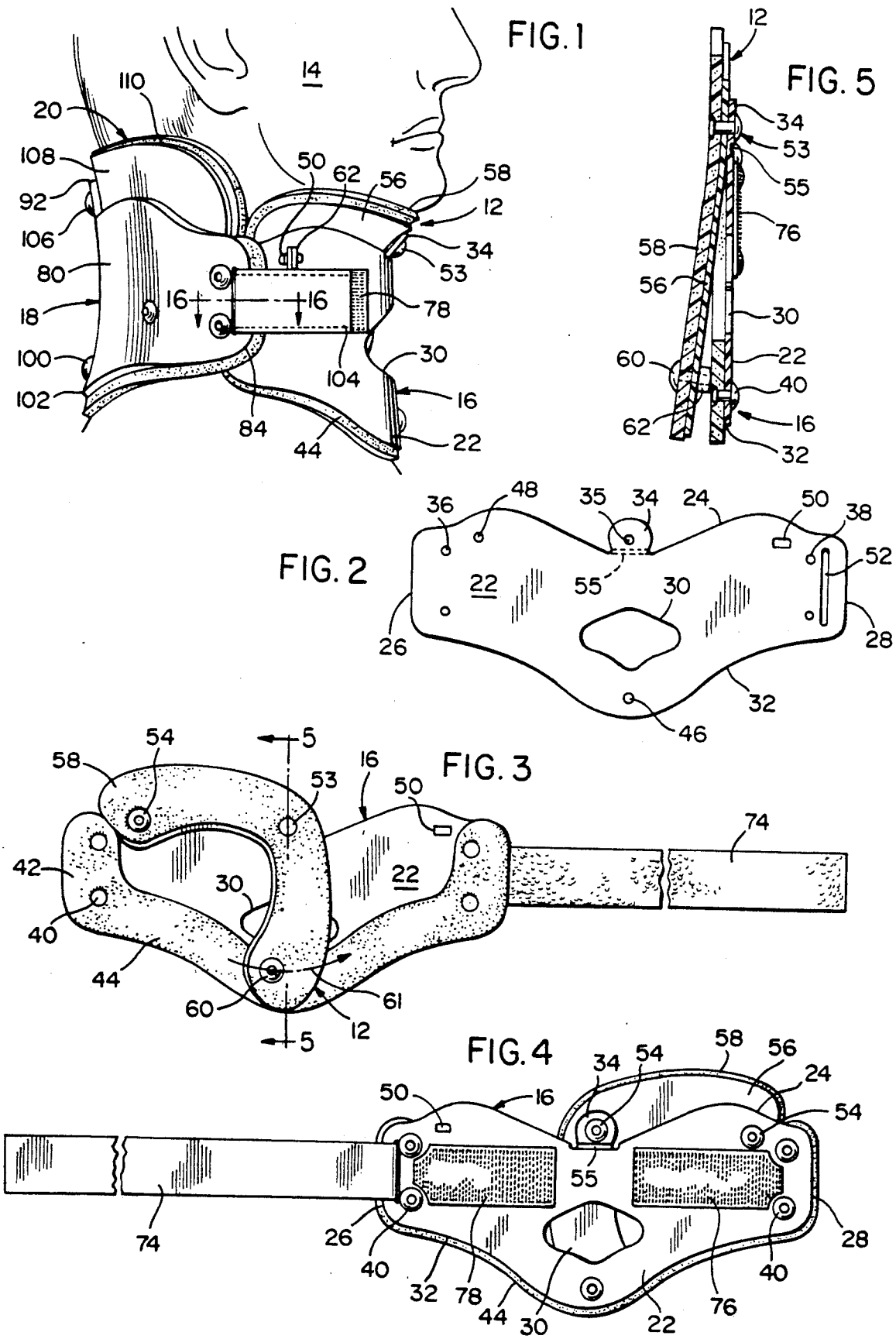

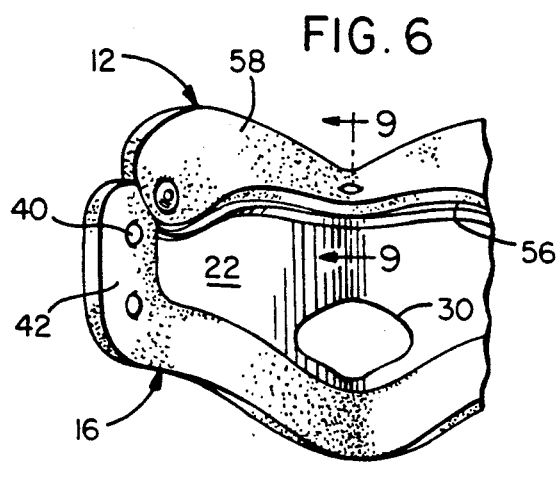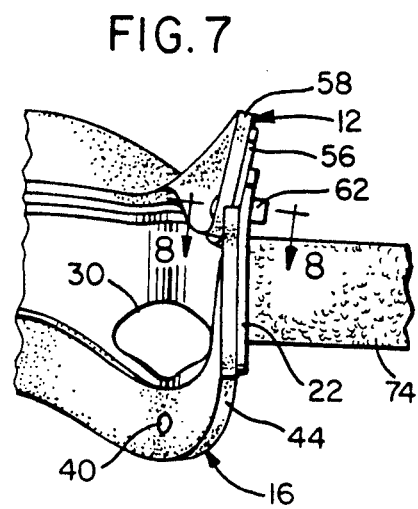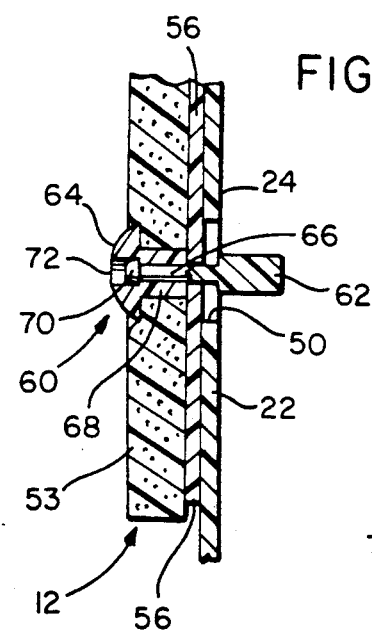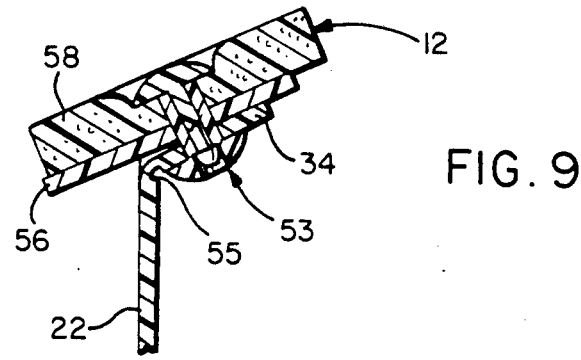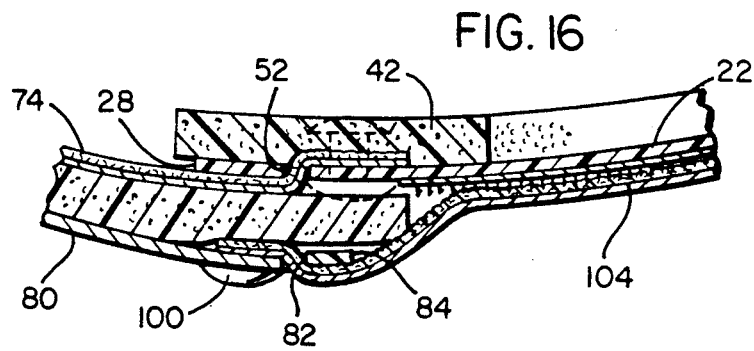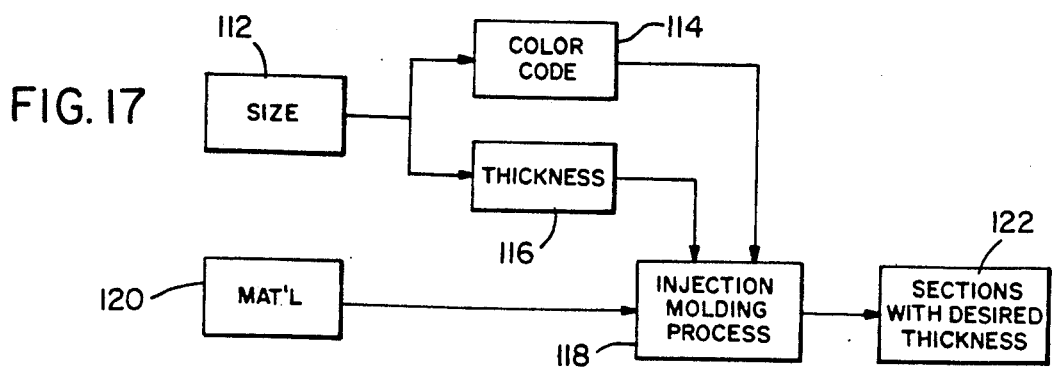

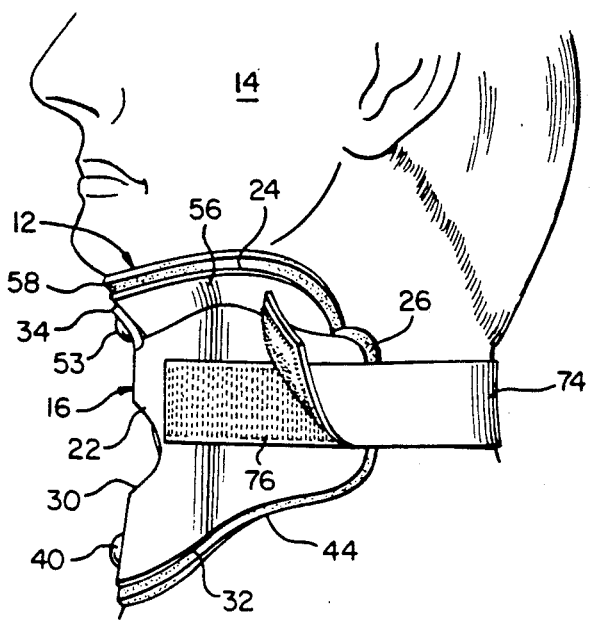
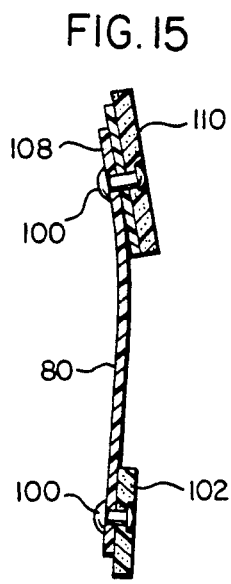
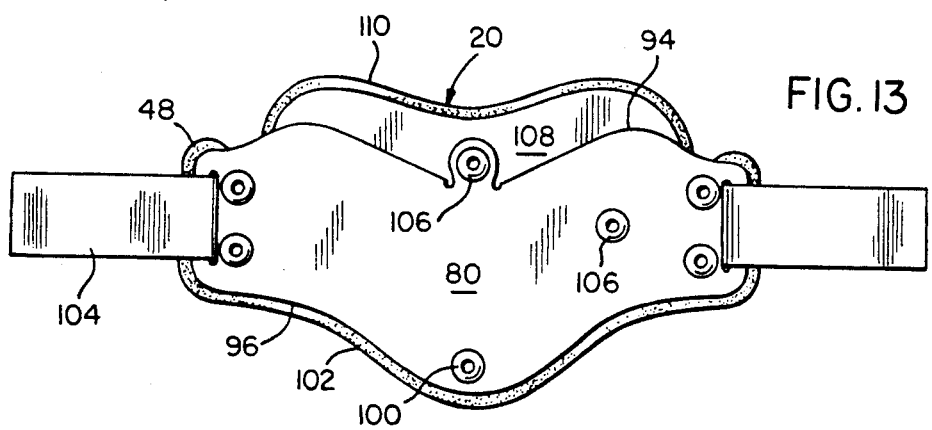
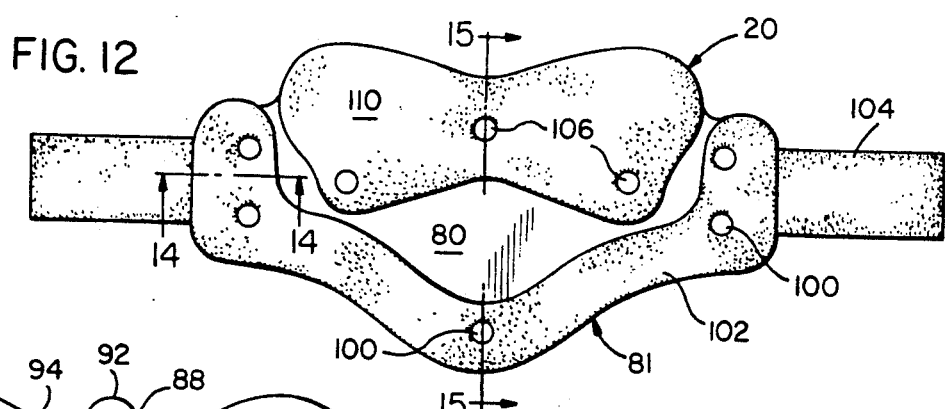
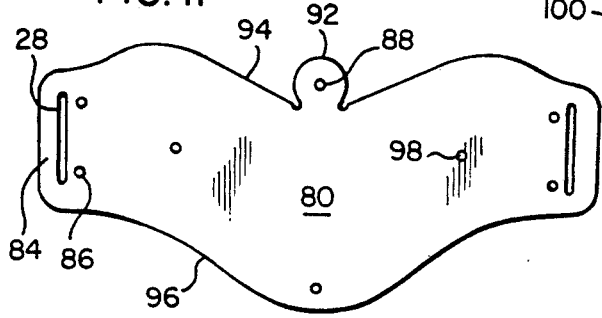
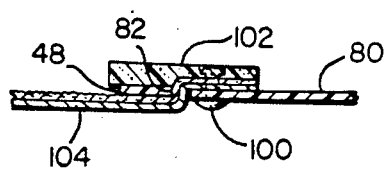

CERVICAL ORTHOPEDIC DEVICE

BACKGROUND OF THE INVENTION

This invention relates to cervical orthopedic devices and, more particularly, to semi-rigid neck braces or collars used in the treatment and therapy of cervical trauma.

Cervical collars having chin immobilizing supports attached thereto are already well known, including collars cut from semi-rigid plastic sheet material with padding mounted thereon. Such a cervical collar is disclosed, for example in, in U.S. Pat. Nos. 4,413,619 and RE32219 to Garth.

The collar disclosed and claimed in the Garth patent features a one-piece, neck-encircling band, the ends of which are held in overlapping relation on one side of the patient's neck by a VELCRO locking arrangement. Because of its one-piece construction from sheet material, the cervical collar covered by the Garth patent presents problems in the provision of collars of different size and stiffness for adaptation to patients in different size groups or categories.

It is therefore an important object of the present invention to provide a cervical collar of the aforementioned type which is more readily adjustable and capable of being made in different sizes in a more economical fashion to accommodate a wider group of patients.

SUMMARY OF THE INVENTION

In accordance with the present invention, a cervical collar is formed by separate front and back sections made of a plastic material that is injection molded to a thickness corresponding to optimum stiffness for a selected size collar. The front section is adjustably positioned by a flexible strap encircling the back of the neck. The back section having a separate stabilizing contact section attached thereto, is fitted about the back of the neck in overlying relation to the flexible positioning strap and overlapping the end portions of the front section on both sides of the neck at which it is releasably locked to the front section. By color coding the injection molded material to identify the collar size, the desired thickness for different size categories is provided in order to accommodate manual bending of the sections to the neck-encircling curvature during installation while providing the desired supporting rigidity when the collar is fully stabilized in adjusted position on the patient.

BRIEF DESCRIPTION OF THE DRAWING FIGURES

These together with other objects and advantages which will become subsequently apparent reside in the details of construction and operation as more fully hereinafter described and claimed, reference being had to the accompanying drawings forming a part hereof, wherein like numerals refer to like parts throughout.

FIG. 1 is a side elevation view of a cervical orthopedic device fitted onto a patient, in accordance with one embodiment of the invention.

FIG. 2 is an elevation face view of a front section band associated with the device shown in FIG. 1.

FIG. 3 is an inner face elevation view of the front section of the device in a flattened condition with which the band shown in FIG. 2 is associated.

FIG. 4 is an outer face elevation view of the front section shown in FIG. 3.

FIG. 5 is an enlarged side section view taken substantially through a plane indicated by section line 5—5 in FIG. 3.

FIG. 6 is an inner face elevation view of the front section of FIG. 3, in a fully assembled curved condition.

FIG. 7 is a side elevation view of the front section shown in FIG. 6.

FIG. 8 is an enlarged partial section view taken substantially through a plane indicated by section line 8—8 in FIG. 7.

FIG. 9 is an enlarged partial section view taken substantially through a plane indicated by section line 9—9 in FIG. 6.

FIG. 10 is a side elevation view of the front section of the device with the chin support attached, being adjustably positioned on the patient.

FIG. 11 is an elevation face view of a back section band associated with the device shown in FIG. 1.

FIG. 12 is an inner face elevation view of the assembled back section of the device, with which the band shown in FIG. 11 is associated.

FIG. 13 is an outer face elevation view of the back section shown in FIG. 12.

FIGS. 14 and 15 are enlarged partial section views taken substantially through planes indicated by section lines 14—14 and 15—15 in FIG. 12.

FIG. 16 is an enlarged partial section view taken substantially through a plane indicated by section line 16—16 in FIG. 1.

FIG. 17 is a block diagram depicting the method of constructing portions of the cervical device illustrated in FIGS. 1-16.

DETAILED DESCRIPTION OF PREFERRED EMBODIMENT

Referring now to the drawings in detail, FIG. 1 shows an assembly of a cervical collar generally referred to by reference numeral 10 and a chin support generally referred to by reference numeral 12, worn by a patient 14. The collar 10 includes a front section 16 and a back section 18. The chin support 12 is attached to the front section 16 in a curved, upwardly inclined condition for contact with the chin of the patient while a stabilizing contact section 20 is attached to the back section 18 and projects upwardly therefrom to stabilize support of the collar 10 on the patient in an adjusted position as will be described in detail hereinafter.

FIGS. 3-5 illustrate the front section 16 of the cervical collar with the chin support 12 attached in a generally flattened condition prior to installation on the patient, while FIG. 2 shows the flat, semi-rigid, wing-shaped band 22 from which the front section 16 is assembled. The band 22 is injection molded from a plastic material and has a generally uniform thickness as more clearly seen in FIG. 5.

With reference to FIG. 2, the plastic band 22 has an upper edge portion 24 extending between opposite longitudinal end portions 26 and 28. A quadrilateral shaped throat access opening 30 is formed in the band midway between the end portions 26 and 28 and spaced from upper edge portion 24 and a lower edge portion 32. An attachment tab 34 projects upwardly from the upper edge portion centrally between the end portions and has a fastener hole 35 therein. Vertically spaced pairs of holes 36 and 38 are formed in the band in spaced adjacency to the end portions 26 and 28, respectively, through which two of three fasteners 40 extend as shown in FIG. 3 to attach end extensions 42 of an elongated foam padding 44 to the band 22. A third fastener 40 centrally attaches the padding 44 to band 22 as shown in FIG. 5, and extends through hole 46 in the band adjacent to the lower edge portion 32 from which the padding projects as shown in FIGS. 4 and 5.

With continued reference to FIG. 2, an additional fastener hole 48 is formed in the band 22 adjacent the upper edge portion 24 closer to the end portion 26 than the central attachment tab 34. On the other side of the tab 34, a slot 50 is formed closer to the end portion 28 and in spaced adjacency to the upper edge portion 24. A vertically elongated slot 52 is formed in the band in parallel spaced relation to the end portion 28 close to and spanning the pair of fastener holes 38, aforementioned. The fastener holes 35 and 48, and the slot 50 are associated with the attachment of the chin support 12 to the band. A recess 55 is formed in one planar face of the band 22 as shown in FIGS. 2, 4 and 5 so as to establish a flexure hinge connection between the attachment tab 34 and the body of the band 22 with which the tab is integrally formed by injection molding.

The chin support 12 is attached by two fasteners 53 and 54 to the band 22 through the hole 48 in the body of the band and the hole 35 in the attachment tab 34 as shown in FIGS. 3 and 5. The fasteners 53 and 54 extend through a semi-rigid arcuate band 56 and foam padding 58 of substantially the same arcuate shape, such band 56 and padding 58 constituting the chin support 12. Thus, the chin support 12 is preassembled with the front section 16 in its flattened condition by attachment thereto at two spaced locations along the upper edge portion through the two fasteners 53 and 54. A third fastener 60 is angularly displaced by bending of section 20 during assembly as indicated by arrow 61 in FIG. 3. The fastener 60 includes a rotatable projection 62, as shown in FIG. 5, to hold the padding 58 attached to the band 56 of the chin support and to releasably connect the chin support to the front section 16 through slot 50 in the band 22 for final assembly therewith, as will be explained hereinafter.

In order to attach the chin support 12 to the front section 16 at the third location along its upper edge portion 24 through slot 50 and fastener 60, both the front section 16 and the chin support 12 must be manually bowed or bent to the curved conditions as shown in FIGS. 6 and 7. The front section 16 and chin support 12 are releasably held in such curved conditions by the fastener assembly 60 which includes a plastic head 64 abutting the padding 58 of the chin support as more clearly seen in FIG. 8. The projection 62 is connected to one end of a shank 66 rotatably extending through sleeve 68 to which the head 64 is connected. A retainer 70 connected to the end of shank 66 opposite projection 62, within opening 72 in head 64, prevents axial separation of the projection 62 from the fastener assembly The projection 62 is of a flat rectangular shape dimensioned to be inserted through slot 50 in the front section band 22 when rotated into alignment therewith. Once inserted through slot 50, the projection 62 is rotated 90 to the position shown in FIG. 8 in order to hold the chin support 12 and front section 16 assembled in their curved conditions as shown in FIGS. 6 and 7.

In their curved conditions, the front section 16 has a neck-encircling curvature so that it may be fitted onto the patient 14 as shown in FIG. 10, with the chin support curvature accommodating comfortable chin supporting contact. Under such assembled conditions, the attachment tab 34 has undergone flexure by approximately 10° relative to the front section band 22, with which it is integrally formed, as more clearly seen in FIG. 9. The flexure hinge establishing recess 55 accommodates such bending without rupture.

The front section 16 of the cervical collar with the chin support attached is adjustably positioned in neck-encircling relation to the patient as shown in FIG. 10 by means of a flexible positioning strap 74. The strap is anchored to end portion 28 of the front section band 22 by means of the fasteners 40 in engagement with the end portion of the strap extending through slot 52 into underlying relation to padding extensions 42. Thus, the strap extends from the outer, non-padded surface of the band 22 at end portion 26, as shown in FIG. 4, and is dimensioned to encircle the back of the patient'snneck and overlap the opposite end portion 28 for contact with a VELCRO locking strip 76 adhesively secured to the non-padded surface of band 22 between opening 30 and the fasteners 40 adjacent end portion 28. The strap 74 is accordingly releasably locked to the front section 16 through VELCRO lock 76 to adjustably position the front section on the patient as shown in FIG. 10.

As shown in FIG. 4, another VELCRO locking strip 78 is secured to the non-padded face of the front section on the other side of opening 30 opposite the VELCRO strip 76. Such VELCRO strip 78 is utilized to lock the back section 18 to the adjustably positioned front section for stabilized support thereof as shown in FIG. 1.

The back section 18 as shown in FIGS. 11-13 includes a semi-rigid plastic band 80 similar in construction and inverted shape to front section band 22, except that it has no throat access opening and is provided with strap anchoring slots 82 adjacent both end portions 84 to form a totally symmetrical arrangement. Vertically spaced pairs of fastener holes 86 are formed adjacent the slots 82 as shown in FIG. 11, in addition to the fastener holes 88 and 90 respectively formed in a central tab 92 projecting from the lower edge 94 and adjacent the upper edge 96 of the back band 80. Intermediate fastener holes 98 are also formed in the band 80 as shown.

The fastener holes 86 and 88 receive therethrough fasteners 100 through which elongated foam padding 102 is attached to the back band 80 along its upper edge 96 and the end portions 84 from which the padding projects as shown in FIGS. 13 and 15. A pair of flexible straps 104 of shorter length than positioning strap 74, are anchored to the respective end portions 84 of the back section through the slots 82 and fasteners 100, similar to the anchoring described with respect to strap 74, and as more clearly seen in FIG. 14. The straps cooperate with both of the VELCRO strips 76 and 78 to releasably lock the back section in place as will be described in detail hereinafter.

The stabilizing contact section 20 hereinbefore referred to in connection with FIG. 1, is attached by three fasteners 106 to the back section 18 through the fastener holes 90 and 98 so as to project upwardly above the lower edge 94 of the back band. When attached to each other by the fasteners 106, the back band 80 and a shell or band 108 of the stabilizing section 20 acquire a preliminary curvature as shown in FIG. 15 of greater radius than the neck-encircling curvature to which the back section is bent when attached to the previously fitted front section 16. The fasteners 106 also mount padding 110 on the same inner face of the stabilizing shell or band 108 as that of back band 80 to which padding 102 is attached as shown in FIGS. 12 and 15. The padding 110 projects somewhat above the upper edge of band 108.

When the back section 18 of the cervical collar, with the stabilizing section 20 attached, is applied to the patient as shown in FIG. 1, the end portions 84 of the back section overlap the end portions 26 and 28 of the front section. Because of the anchoring arrangements respectively provided for by the slots 52 and 82 for the straps 74 and 104 at the overlapping end portions of the front and back sections, as more clearly seen in FIG. 16, a snug fit is obtained at the occipital bones where the underlying padding extensions 42 are in contact with the patient.

It will be apparent from the foregoing description that the plastic bands 22, 80, 108 and 56 of the front and back sections, the stabilizing section and the chin support, respectively, must have the requisite flexibility to accommodate manual bending to the specified curvatures which are maintained without rupture, and yet afford the necessary stiffness for patient support. Such stiffness property is a function of the thickness of the bands as well as the plastic material itself. Furthermore, the thickness will depend on the selected size of the cervical collar for any given patient. An important aspect of the present invention therefore resides in tailoring the stiffness property of the plastic bands for a plurality of different sizes of cervical collars made available for patients in an economical fashion to provide optimum fit. As diagrammed in FIG. 17, a selection of size as denoted by 112 is identified by a color code 114 from which the color of a material dye is determined. Also, the thickness of the bands is determined from the selected size as denoted at 116 to provide optimum stiffness to meet the objectives aforementioned. Both of such determinations of dye color and thickness are made possible by use of an injection molding process 118 to which the plastic material 120 is fed in order to form the sections of the collar diagrammed at 122 with the optimum stiffness and the color coding for the selected size. Thus, the use of an injection molding process in making the collar is of significant import and of additional benefit in other respects, such as the formation of the hinge recess 55 in the front section band 22 and other structural features.

The foregoing is considered as illustrative only of the principles of the invention. Further since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed is:
1. A cervical collar for a patient, said cervical collar comprising:
separate front and back sections made of plastic material having a stiffness property accommodating bending thereof to a neck-encircling curvature,
a chin support,
means attaching the chin support in a curved condition to the front section for maintaining the neck-encircling curvature of the front section,
flexible strap means connected exclusively to the front section for adjustable positioning of the front section in a neck-encircling relation to the patient with the chin support attached, and means for releasably locking the back section to the front section in overlapping relation thereto and overlying the flexible strap means to support he collar in said adjustably positioned neck-encircling relation to the patient.

2. The cervical collar of claim 1, further comprising contacting means attached to the back section for stabilizing said support of the back section on the patient.

3. The cervical collar of claim 2, wherein aid contacting means including a padded shell and fastening means attaching the padded shell in a curved condition to the back section for establishing a preliminary curvature thereof of greater radius than that of the neck-encircling curvature, said back section being deformed from the preliminary curvature to the neck-encircling curvature in response to said releasable attachment of the back section to the front section.

4. The cervical collar of claim 3, wherein the front section includes a padded band having an upper edge portion, said attaching means for the chin support being mounted at spaced locations along the upper edge portion and including at least one attachment tab projecting from the upper edge portion at one of said spaced locations.

5. The cervical collar of claim 4, wherein the padded band is formed with a recess at said one of the spaced locations from which the attachment tab projects to establish a flexure hinge.

6. The cervical collar of claim 1, wherein the front section includes a padded band having an upper edge portion, said attaching means for the chin support being mounted at spaced locations along the upper edge portion and including at least one attachment tab projecting from the upper edge portion at one of said spaced locations.

7. The cervical collar of claim 6, wherein the padded band is formed with a recess at said one of the spaced locations from which the attachment tab projects to establish a flexure hinge.

8. The cervical collar of claim 1, wherein the front section is color coded in accordance with the size of the collar.

9. The cervical collar of claim 2, wherein each of said front and back sections have upper and lower edge portions and opposite end portions, said chin support being attached by the attaching means to the upper edge portion of the front section while the contacting means attached to the back section projects from the upper edge portion thereof, and padding means attached to the lower edge portions of the front and back sections for cushioning contact with the patient, extensions of said padding means extending from the flower edge portions of the front and back sections, respectively, along the opposite end portions thereof, said releasable locking means holding the opposite end portions of the back section in said overlapping relationship to the opposite end portions of the front section cushioned by the extensions of the padding means on occipital bone areas of the patient.

10. The cervical collar of claim 9, further comprising fastener means securing the extensions of the padding means to the opposite end portions of the from and back sections for holding the padding means on the front and back sections along the lower edge portions thereof, respectively.

11. A cervical collar for a patient, said cervical collar comprising separate front and back sections made of plastic material having a stiffness property accommodating bending thereof to a neck-encircling curvature, flexible strap means connected exclusively to the front section for adjustable positioning of the front section in a neck-encircling relation to the patient, means for releasably locking the back section to the front section in overlapping relation thereto overlying the flexible strap means to support he collar in said neck-encircling relation to the patient, and contact means attached to the back section for stabilizing said support of the collar on the patient.

12. The cervical collar as defined in claim 11, wherein said contact means includes a padded shell and fastening means attaching the padded shell in a curved condition to the back section for establishing a preliminary curvature thereof of greater radius than that of the neck-encircling curvature, said back section being deformed from the preliminary curvature to the neck-encircling curvature in response to said releasable attachment thereof to the front section.

13. A cervical collar assembly comprising
an neck-encircling portion,
a chin support attached to said neck-encircling portion, said neck-encircling portion including separate semi-rigid supporting sections,
flexible strap means connected exclusively to one of the supporting sections, said flexible strap means extending in an underlying relation to the other of the supporting sections for adjustably positioning the collar,
stabilizing means projecting from said other of the supporting sections for stabilized support of the collar adjustably positioned by the flexible strap means,
padding means on said supporting sections for cushioning contact, and
fastener means for mounting the padding means on the supporting sections.

14. The cervical collar of claims 13, wherein said supporting sections include lateral overlapping portions through which the fastener means extend and means for releasably locking said lateral overlapping portions of the supporting sections to each other.

15. The cervical collar of claim 14, wherein said supporting sections are made of injection molded plastic material.

16. The cervical collar of claim 13, wherein said supporting sections are made of injection molded plastic material.

* * * * *